United States Patent
Ueno et al.

(10) Patent No.: US 6,849,742 B2
(45) Date of Patent: Feb. 1, 2005

(54) BINAPHTHOL DERIVATIVE AND PROCESS FOR PRODUCING THE SAME

(75) Inventors: Ryuzo Ueno, Nishinomiya (JP); Masaya Kitayama, Takarazuka (JP); Kenji Minami, Sennan (JP); Hiroyuki Wakamori, Hikami-gun (JP)

(73) Assignee: Kabushiki Kaisha Ueno Seiyaku Oyo Kenkyujo, Osaka (JP)

( * ) Notice: Subject to any disclaimer, the term of this patent is extended or adjusted under 35 U.S.C. 154(b) by 0 days.

(21) Appl. No.: 10/250,442

(22) PCT Filed: Apr. 18, 2002

(86) PCT No.: PCT/JP02/03850

§ 371 (c)(1),
(2), (4) Date: Jul. 1, 2003

(87) PCT Pub. No.: WO02/085836

PCT Pub. Date: Oct. 31, 2002

(65) Prior Publication Data

US 2004/0063963 A1 Apr. 1, 2004

(30) Foreign Application Priority Data

Apr. 19, 2001 (JP) ........................................ 2001-120973

(51) Int. Cl.$^7$ ............................................. C07D 277/62
(52) U.S. Cl. .................... 548/156; 548/220; 548/305.4; 560/21; 560/45; 560/56; 562/435; 562/455; 562/467; 564/153; 564/156
(58) Field of Search ............................... 548/156, 220, 548/305.4; 560/21, 45, 56; 562/435, 455, 467; 564/153, 156

(56) References Cited

U.S. PATENT DOCUMENTS 3,278,610 A  10/1966  Butte et al.

FOREIGN PATENT DOCUMENTS

| JP | 62-77341 A | 4/1987 |
| JP | 6-145086 A | 5/1994 |
| JP | 8-20552 A | 1/1996 |
| JP | 10-204015 A | 8/1998 |

OTHER PUBLICATIONS

Nakajima, M. et al., Enantioselective Synthesis of Binaphthol Derivatives by Oxidative Coupling of Naphtol Derivatives Catalzed by Chiral Diaine–Copper Complex., J. Org. Chem., vol. 64, No. 7 (1999), pp. 2264 to 2271.

Taiwanese Office Action dated Sep. 6, 2004 in a corresponding application.

Primary Examiner—Bernard Dentz
(74) Attorney, Agent, or Firm—Sughrue Mion, PLLC

(57) ABSTRACT

The present invention provides a binaphthol compound represented by formula [1]:

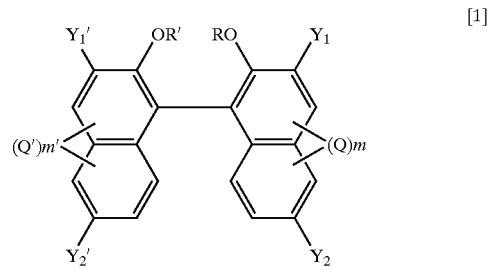

and a salt thereof. The binaphthol compound of the present invention is useful for manufacturing antiseptic compounds or chiral catalysts. According to the method of the present invention, binaphthol compounds can be prepared in high yield with low cost.

13 Claims, 8 Drawing Sheets

BINAPHTHOL DERIVATIVE AND PROCESS FOR PRODUCING THE SAME

This application is a National Stage Application of PCT/JP02/03850 filed Apr. 18, 2002.

TECHNICAL FIELD

The present invention relates to a binaphthol derivative having carboxyl groups or others at 3- and 6-positions of the naphthalene rings, and a method for preparing the same.

BACKGROUND ART 1,1'-bi-2-naphthol, a compound obtainable by dimerization of β-naphthol or its derivative, is useful for preparing an antiseptic compound or an asymmetric synthesis catalyst.

In addition, dimers of 2-hydroxynaphthalene-3-carboxylic acid and of 2-hydroxynaphthalene-6-caboxylic acid are useful as toning agents.

U.S. Pat. No. 3,278,610 discloses a method for preparing said dimer, which comprises dimerising β-naphthol in a solvent such as benzene in the presence of copper chloride, amine and oxygen.

J. Org. Chem. 1999, 64, 2264–2271 discloses a method for dimerizing β-naphthol or the like, which comprises oxidative coupling of p-naphthol, methyl 2-hydroxynaphthalene-3-carboxylate or the like in the presence of copper (I) chloride-tetramethylethylenediamine complex in dichloromethane, wherein copper (I) chloride and tetramethylethylenediamine are combined before the coupling reaction.

Conventional methods for preparing binaphthol derivatives require a solvent, such as benzene or dichloromethane, to dissolve β-naphthol or the like therein to facilitate the coupling reaction, and the solvent causes high cost. Further, the method of J. Org. Chem. 1999, 64, 2264–2271 is complicated because the method comprises the extra step of combining copper (I) chloride and tetramethylethylenediamine prior to the coupling reaction.

DISCLOSURE OF THE INVENTION

One object of the present invention is to solve the above problems and to provide a method for preparing a binaphthol derivative in high yield with low cost.

Another object of the present invention is to provide a novel binaphthol derivative.

Further object of the present invention is to provide an optically active binaphthol derivative, which is useful for preparing an asymmetric catalyst.

Accordingly, the present invention provides a binaphthol derivative represented by the formula [I]:

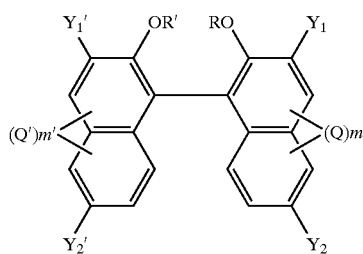

wherein $Y_1$, $Y_1'$, $Y_2$, and $Y_2'$ may be same or different and each is selected from the group consisting of a carboxyl group, an esterified carboxyl group, a group of —(CONH)n-X wherein X is an optionally branched and optionally substituted hydrocarbon group which may have an unsaturated bond, an optionally substituted aromatic group or a heterocyclic group having conjugated double bonds, n is an integer of 1 or 2, and a group of formula [2]

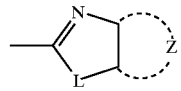

wherein L is —O—, —S— or —NH—, and Z is an optionally substituted aromatic group or a heterocyclic group having conjugated double bonds;

R and R' are selected from the group consisting of hydrogen atom, an alkaline metal, an optionally branched and optionally substituted alkyl group of 1–20 carbon atoms, an acyl group and a phenylalkylene group;

Q and Q' are selected from the group consisting of optionally branched alkyl and alkoxy group of 1–6 carbon atoms, a halogen atom, nitro group or nitroso group; and m and m' each represents an integer of 0–3 or a salt thereof.

In the above formula [1], examples of preferable esterified carboxyl groups of $Y_1$, $Y_1'$, $Y_2$ and $Y_2'$ include halogeno carboxyl groups such as bromocarbonyl and chlorocarbonyl, alkoxycarbonyl of 1–6 carbon atoms, such as methoxycarbonyl, ethoxycarbonyl, propyloxycarbonyl, isopropyloxycarbonyl, pentyloxycarbonyl and hexyloxy carbonyl, phenoxycarbonyl and phenacyloxycarbonyl. In case the group has an aromatic moiety, said moiety may have a substituent.

Examples of the optionally branched and optionally substituted hydrocarbon group which may have an unsaturated bond of X may include alkyl of 1–20 carbon atoms such as ethyl, butyl, octyl, dodecyl and octadecyl, alkenyl of 2–6 carbon atoms such as vinyl, allyl and pentenyl. Examples of the optionally substituted aromatic group of X may include, for example, phenyl, naphthyl, anthryl, anthraquinonyl and pyrenyl. Examples of the optionally substituted heterocyclic group having conjugated double bonds of X may include, for example, thiofuryl and furyl.

In the group of formula [2], examples of the optionally substituted aromatic group of Z may include benzene, naphthalene and anthraquinone. Examples of the optionally substituted heterocyclic group moieties may include thiophene, furan, pyrrole, imidazole, pyrazole, isothiazole, isoxazole, pyridine, pyrazine, pyrimidine, pyridazine, triazole, tetrazole, indole, 1H-indazole, purine, 4H-quinolizine, isoquinoline, quinoline, phthalazine, naphthylidine, quinoxaline, quinazoline, cinnoline, pteridine and benzofuran. Examples of the groups represented by formula [2] may include benzimidazole, benzoxyazole and benzothiazole.

Examples of substituents in each definition may include halogen atom, halogenated lower alkyl, nitro, lower alkyl, lower alkoxy such as methoxy, cyano, phenyl, naphthyl, phenoxy, furyl, amino, toluidylamino, triazylamino, pyridylamino, benzoylamino, hydroxy, esterified carboxyl group such as alkoxycabonyl and phenoxycarbonyl, amidized carboxyl groups such as phenylcarbamoyl group, alkylaminosulfonyl group, alkenyl group of 2–6 carbon atoms which may include aryl group.

When the substituent contains an aromatic ring, the compound may further have one or more substituents such as a halogen atom, a lower alkyl, a lower alkoxy, phenyl, and nitrile groups on said aromatic ring.

In the present specification and claims, "lower" represents a group having 1–6 carbon atoms.

"Aromatic group" represents a 6-membered monocyclic aromatic group or condensed ring group consisting of up to 4 of 6-membered aromatic rings.

"Heterocyclic group having conjugated double bonds" represents a 5- or 6-membered mono-cyclic group or condensed ring group having at least one hetero-atom selected from N, S and O and conjugated double bonds. When it represents a condensed ring group, said group may have up to 6 rings.

In the present invention, each of the two naphthalene nuclei of the binaphthol derivative represented by formula [1] may have substituents of Q or Q' respectively. Each of Q and Q' may independently represent an optionally branched alkyl or alkoxy group of 1–6 carbon atoms, a halogen atom, nitro group or nitroso group.

Each of m and m', which represents the number of the substituent, is usually 0 and may be up to 3.

Examples of R and R' may include hydrogen atom, an alkaline metal, optionally branched and optionally substituted alkyl and acyl groups each having 1–20 carbon atoms and a phenylalkylen group such as benzyl group.

Among the binaphthol derivatives represented by formula [1], the present invention especially provides a binaphthol derivative of formula [3] below having substituents other than free carboxyl group at both 3- and 6-positions of the naphthol rings.

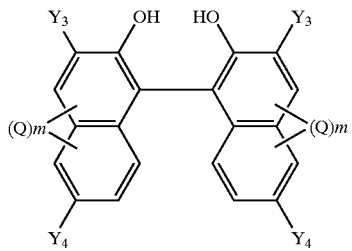

[3]

wherein $Y_3$ and $Y_4$ may be same or different and each is independently selected from the group consisting of an esterified carboxyl group and a group of —(CONH)n-X, wherein X and n are the same as defined above; and Q and m are the same as defined above.

In the general formula [3], $Y_3$ and $Y_4$ may be esterified carboxyl groups or groups of —(CONH)n-X at the same time. Alternatively, one of $Y_3$ and $Y_4$ may be an esterified carboxyl group and the other may be —(CONH)n-X.

Examples of esterified carboxyl groups of $Y_3$ and $Y_4$ may be those described for formula [1].

According to the invention, a compound of formula [1] wherein at least one of the substituents at -3 and -6 positions on respective naphthalene rings is carboxyl group, that is, a binaphthol derivative represented by formula [4] is preferably provided.

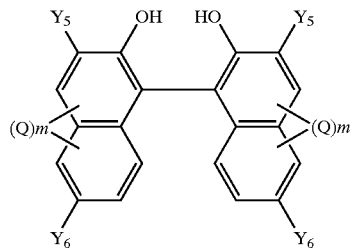

[4]

wherein one of $Y_5$ and $Y_6$ is a carboxyl group and the other is selected from the group consisting of a carboxyl group, an esterified carboxyl group and a group of —(CONH)n-X (wherein X and n are the same as defined above).

In addition, the present invention provides a method for preparing a compound of formula [3]. Accordingly, the present invention provides a method for preparing a binaphthol derivative represented by formula [3]

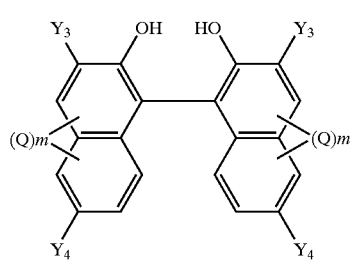

[3]

wherein $Y_3$, $Y_4$, Q and m are the same as defined above characterized in that carrying out oxidative coupling reaction of a naphthol derivative represented by formula [5]

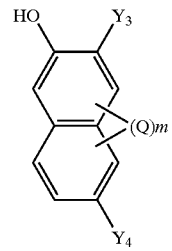

wherein $Y_3$, $Y_4$, Q and m are the same as defined above in a nitrogen containing polar solvent in the presence of a copper salt.

The reason why the present method can provide the binaphthol derivative in high yield may be that the copper salt reacts with the hydroxy group of the formula [5] naphthol, the nitrogen containing polar solvent and oxygen to provide a complex having oxidizing ability, and the complex affects as a catalyst to promote the oxidative coupling reaction of the instant invention.

Examples of copper salts used in the present invention may include copper(I) chloride, copper(II) chloride, copper (I) bromide, copper(II) bromide, copper(I) iodide, copper(II) acetate and copper (II) formate. Copper(I) chloride is most preferable among them, since its catalytic ability is recovered by oxygen during the reaction and accordingly the amount of the copper salt used in the reaction can be reduced.

When copper(I) chloride is used, it is recommendable to supply air or oxygen actively into the reaction.

The amount of copper salt used in the reaction may be 0.5–100 mole, preferably, 5–10 mole per 100 mole of the formula [5] naphthol derivative.

When the amount of copper salt is less than 0.5 mole per 100 mole of the naphthol derivative, the reaction speed may become very slow, and when the amount is more than 100 mole, an unfavorable side reaction may occur.

In the method of the instant invention, the nitrogen containing polar solvent is used as a reaction medium to facilitate the reaction and also as a ligand which forms a complex having an oxidative ability with the copper salt. Preferable nitrogen containing polar solvents may be those represented by formulae [6] and [7].

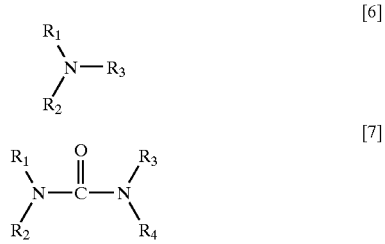

wherein $R_1$, $R_2$, $R_3$ and $R_4$ may be same or different and each independently selected from the group consisting of formyl, alkyl, alkenyl, acyl and optionally substituted phenyl groups.

In the above formulae, $R_1$, $R_2$, $R_3$ and $R_4$ may be same or different and each independently represents formyl group, an alkyl group of 1–6 carbon atoms such as methyl, ethyl, propyl and hexyl groups; an alkenyl group of 2–6 carbon atoms such as vinyl, allyl and pentenyl groups, an acyl group of 1–6 carbon atoms such as acetyl group and an optionally substituted phenyl group.

Examples of the substituent may include a halogen atom, a halogenated lower alkyl, nitro, a lower alkyl, a lower alkoxy such as methoxy, cyano, phenyl, naphthyl, phenoxy, furyl, amino, toluidylamino, triazylamino, pyrimidylamino, benzoylamino, hydroxy, esterified carboxyl such as alkoxycarbonyl and phenoxycarbonyl, amidated carboxyl such as phenylcarbamoyl, alkylaminosulfonyl and alkenyl of 2–6 carbon atoms which may contain an aryl.

When the substituent contains an aromatic ring, the compound may further have one or more substituents such as halogen atom, lower alkyl, lower alkoxy, phenyl and nitrile on said aromatic ring.

Examples of the solvent represented by formula [6] may include N,N-dimethylformamide, N,N-dimethylacetamide, N,N-diethylacetamide, N,N-dimethylpropylamide, N,N-dimethylacetanilide, N,N-dimethylaniline and N,N-dimethylanisidine. Examples of solvent represented by formula [7] may contain tetramethyl urea and tetraethyl urea.

Preferable nitrogen containing polar solvent may include N,N-dimethylformamide, N,N-dimethylacetamide, N-methyl-2-pyrrolidone, morpholine, N-methylmorpholine, N,N-diethylacetamide, N,N-dimethylpropylamide, tetramethyl urea, tetraethylurea, N-methylacetanilide, N,N-dimethylaniline, N,N-dimethylanisidine, pyridine, and 2-methylpyridine. Especially, N,N-dimethylformamide, N,N-dimethylacetamide and N,N-methyl-2-pyrrolidone are preferable since they can dissolve the ester or amide derivative of 2-hydroxynaphthalene-3,6-dicarboxylic acid well.

An amount of the nitrogen containing polar solvent enough to dissolve the naphthol derivative of formula [5] may be used for the reaction. Typically, the amount may be 5–50, preferably, 5–30 fold by weight of the formula [5] naphthol derivative.

The method for preparing a compound represented by formula [3] according to the instant invention may be carried out as follows.

Firstly, the naphthol derivative represented by formula [5] is dissolved or dispersed in a nitrogen containing polar solvent at room temperature. A copper salt is added thereto and the obtained reaction mixture is then heated to 40–120° C., preferably 60–80° C. under pressure or under an ambient pressure to effect oxidative coupling reaction to give the binaphthol derivative represented by formula [3].

The duration of the oxidative coupling reaction may be determined depending on the amount of the catalyst and the reaction temperature and normally, may be 1–48 hours. The completion of the reaction may be confirmed by disappearance of the starting material in the reaction mixture, which can be monitored with HPLC or the like.

After the oxidative coupling reaction is completed, the reaction solution or that admixed with water may be filtrated, washed and, if desired, recrystalized to give crystalline binaphthol derivative of formula [3] in high purity.

An attempt to obtain a binaphthol derivative represented by formula [4] by means of oxidative coupling of the formula [5] naphthol derivative wherein $Y_3$ and/or $Y_4$ are carboxyl groups in a nitrogen containing polar solvent in the presence of a copper salt will fail because the copper salt bounds to the carboxyl group to prevent complex formation. In such a situation, no oxidative coupling reaction occurs and therefore, the above embodiment cannot be employed for preparation of the binaphthol derivative represented by formula [4].

As a result of the instant inventors study, a binaphthol derivative of formula [4] can be obtained by hydrolyzing the binaphthol derivative of formula [3] which can be obtained by means of the oxidative coupling reaction.

Accordingly, the present invention further provides a method for preparing a binaphthol derivative represented by formula [4] comprising the step of hydrolyzing a binaphthol derivative represented by formula [3].

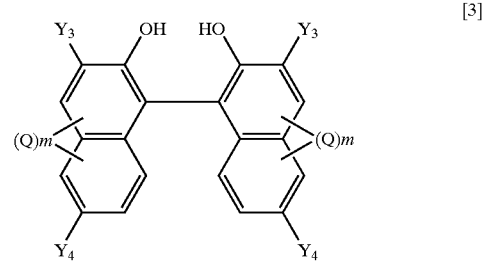

wherein $Y_3$, $Y_4$, Q and m are the same as above defined, provided that $Y_3$ and $Y_4$ are not —(CONH)n-X at the same time.

In this embodiment of the present invention, the step of hydrolyzing the formula [3] binaphthol derivative may preferably be carried out in a basic solution on heating. More precisely, the binaphthol derivative of formula [3] may be dissolved in an organic solvent, such as methanol, and an alkaline solution, such as aqueous sodium hydrate, may be added thereto and heated to 40–100° C. to hydrolyze the esterified carboxylic group. After that, the binaphthol derivative of formula [4] may be obtained by treating the reaction with hydrochloride or the like.

Further, the binaphthol derivative of formula [1] wherein $Y_1$, $Y_1'$, $Y_2$ and $Y_2'$ are the group represented by formula [2], i.e. the binaphthol derivative of formula [10] can be obtained, for example, by the reaction shown in scheme 1.

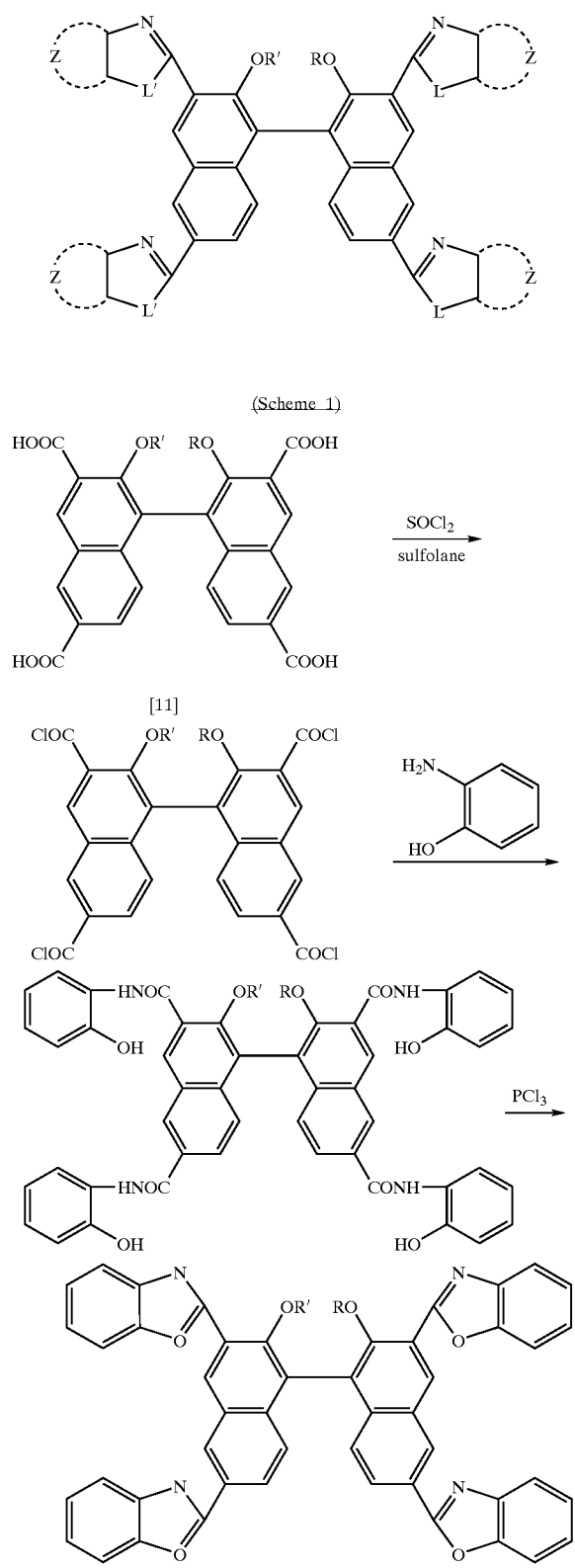

(Scheme 1)

Then the excess thionyl chloride is distilled off. Then, a compound of formula [12]

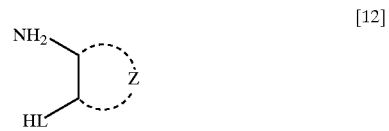

wherein L and Z represent the same as above defined is added thereto.

Examples of compounds represented by formula [12] may include 2-aminophenol, 2-aminothiophenol, 2-amino-4-nitrophenol, 2-amino-5-nitrophenol, 2-amino-4-chloro-5-nitrophenol, 2-amino-4-chlorophenol, 2-amino-4-methylphenol, 2-amino-3-hydroxypyridine, 2-amino-3-hydroxynaphthalene, 2-amino-3-hydroxyanthraquinone, 2-amino-5-methylphenol, 1-amino-2-hydroxynaphthalene, 2-amino-1-hydroxynaphthalene, o-phenylenediamine, 4-methoxy-1,2-phenylenediamine, 4-nitro-1,2-phenylenediaminie, 4-chloro-1,2-phenylenediamine and 4,5-dichloro-1,2-phenylenediamine.

After that, phosphorus trichloride or the like is added to the mixture, the mixture is reacted at 120–140° C., and the reaction is poured in water and then filtered to collect precipitates to give binaphthol derivative of formula [10].

Alternatively, the same compound can be obtained, without thionyl chloride, by reacting the binaphthol derivative of formula [11] and the compound [12] in sulfolane in the presence of phosphorous trichloride or the like.

An attempt to obtain a binaphthol derivative of the instant invention represented by formula [1] wherein R and R' are selected from the group consisting of an alkali metal, an optionally branched and optionally substituted alkyl group of 1–20 carbon atoms, an acyl group and a phenyl alkylene group, by means of oxidation coupling reaction of the naphthol derivative of formula [5] which has a substituent other than hydroxy at the 2-position in a nitrogen containing polar solvent in the presence of a copper salt will fail, because the copper salt cannot form a complex with the substituent other than hydroxy group and therefore the oxidative coupling reaction is prevented.

Alternatively, a binaphthol derivative of formula [3], that is, a binaphthol derivative having hydroxy groups at the 2-positions of both naphthol rings, may be prepared firstly according to the instant invention. And then, the binaphthol derivative of formula [3] may be dissolved in a solvent such as N,N-dimethylformamide, and reacted with an appropriate halogenated alkyl in the presence of potassium carbonate or the like to provide the desired compound. For example, a binaphthol derivative of formula [1] wherein R and R' are methyl groups may be synthesized according to the reaction below (scheme 2):

Accordingly, the binaphthol derivative of formula [11] is dispersed in sulfolane, N,N-dimethylformamide is added thereto and the derivative is reacted with thionyl chloride.

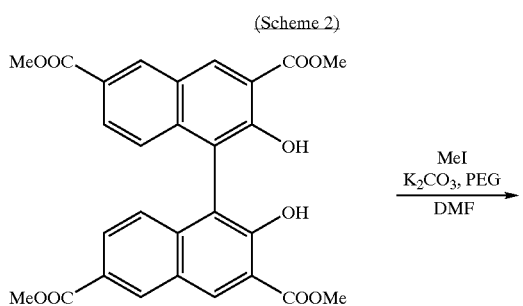

(Scheme 2)

-continued

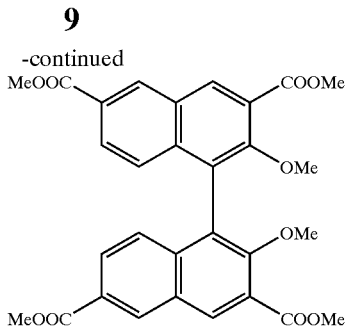

wherein Me is methyl, PEG is polyethylene glycol, DMF is N,N-dimethylformamide.

The naphthol derivative of formula [5], which is especially useful for the method of the instant invention, may be obtained by the following method:

Firstly, 2-hydroxynaphthalene-3,6-dicarboxylic acid may be obtained by the process according to WO98/17621 (Japanese patent Application No. 10–519205), that is, by reacting potassium 2-naphtholate and carbon dioxide, acidifying out the reaction to obtain the compound and, if desired, purifying the obtained compound.

Then, an acid chloride of thus obtained 2-hydroxynaphthalene-3,6-dicarboxylic acid may be prepared by reacting with thionyl chloride or the like in a solvent such as xylene and sulfolane in a conventional manner, and then, may be treated with an amine to give the amide compound. Alternatively, 2-hydroxynaphthalene-3,6-dicarboxylic acid may be reacted directly with an amine in the presence of phosphorus trichloride or dicyclohexylcarbodiimide to give the amide compound.

An ester compound of formula [5] may be obtained by a conventional method, for example, by heating 2-hydroxynaphthalene-3,6-dicarboxylic acid in an alcohol in the presence of an acid catalyst.

Further, a compound of formula [5] wherein one of the substituents at 3- and 6-positions is an ester and the other is an amide may be obtained from 2-hydroxynaphthalene-3,6-dicarboxylic acid by means of the method described in WO96/32366. That is, condensation reaction of the naphthol derivative, 2-hydroxynaphthalene-3,6-dicarboxylic acid 3- or 6-mono ester and an aniline compound may be carried out. After that, water may be added thereto and then the reaction mixture may be neutralized and filtrated to give the desired compound.

Generally, the present binaphthol derivative of formula [1] is obtained as a mixture of optical isomers. The respective optically active enantiomers may be used for preparing chiral catalyst for asymmetric synthesis. Accordingly, the present invention also provides optically active binaphthol derivative selected from those represented by formula [8]:

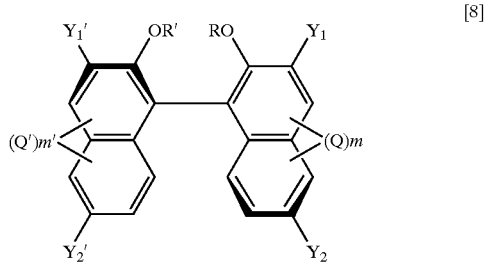

[8]

and formula [9]:

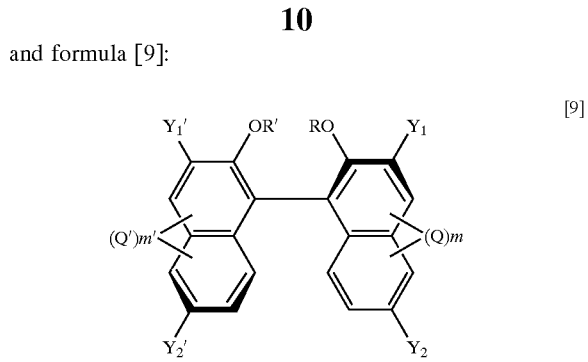

wherein $Y_1$, $Y_1'$, $Y_2$, $Y_2'$, R, R', Q, Q', m and m' are the same as above defined, and a method for preparing the same.

The optically active binaphthol derivative of formula [8] or [9] can be obtained by optical resolution of the binaphthol derivative represented by formula [1]. Optical resolution may be carried out by means of high performance liquid chromatography with optically active column. The process of optical resolution with optically active column chromatography is well known to the art.

According to the oxidation coupling reaction described in the present invention, a binaphthol derivative having an esterified carboxyl group, a group of —(CONH)n- or others at 3- and/or 6-positions of the naphthalene rings can be easily prepared. The optically active binaphthol derivative of formula [8] or [9] is useful for preparing a chiral catalyst for asymmetric synthesis.

The present invention is further described in reference to the following examples. The following examples are intended to illustrate the invention and are not to be construed to limit the scope of the invention.

EXAMPLE 1

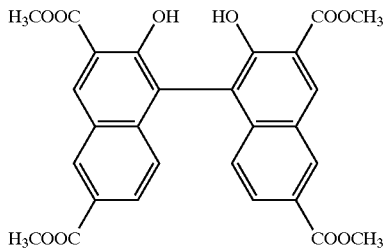

2.6 g of 2-hydroxy-3,6-dimethoxycarbonyl naphthalene was dissolved in 70 g of N,N-dimethylformamide, and 0.1 g of copper(I) chloride was added thereto, and the mixture was stirred at 60° C. The solution was heated for about 48 hours under aeration. Then the reacted solution was poured into 200 g of water and the precipitates were collected by filtration. The obtained precipitates were washed well with methanol and water, and dried to give 1.8 g of the desired compound as white-orange powder (melting point: 310° C., decomposition point:318° C., MS:m/z 517(MW=518.5)).

Figure 1:
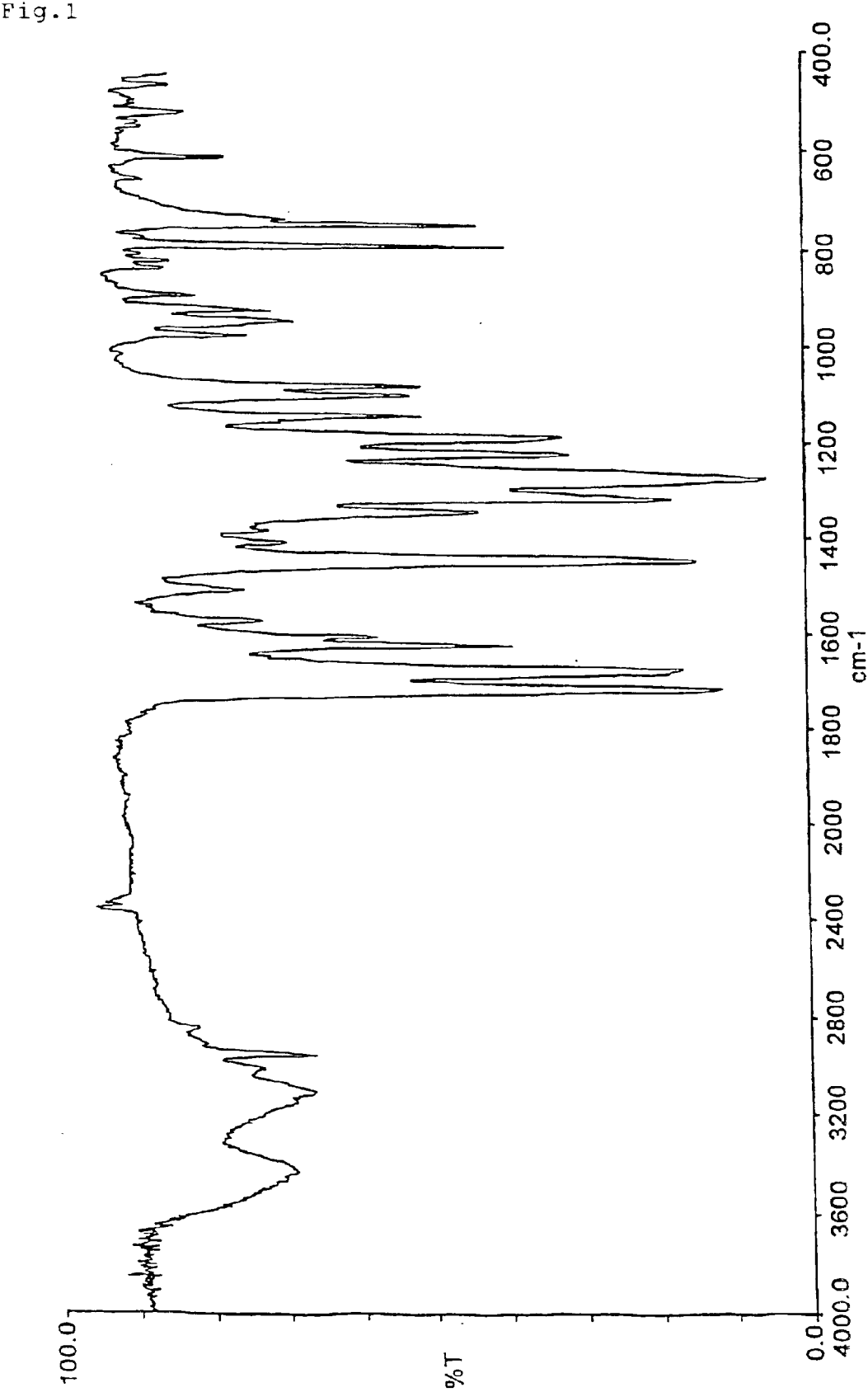
FIG. 1 is an infrared absorption spectrum (KBr) of the binaphthol derivative obtained in Example 1.

The infrared absorption spectrum (KBr) of the same is shown in FIG. 1.

EXAMPLE 2

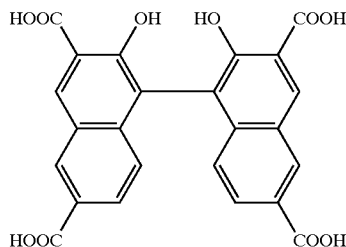

1.6 g of 1,1'-bis(2-hydroxy-3,6-dimethoxycarbonyl naphthalene) obtained in Example 1 was suspended in 20 g of methanol and 20 g of water, and 0.75 g of sodium bicarbonate was added thereto. The mixture was reacted for 5 hours at about 65° C. under reflux. The filtrate was diluted with 40 g of water, the insoluble matter was removed and then, pH of the filtrate was adjusted to 2 with dilute hydrochloric acid. The precipitates were collected by filtration, washed well with water and methanol, and dried to give 1.34 g of the desired compound as pale yellow powder (decomposition point: 407° C., MS: m/z 461 (MW=462.4)).

Figure 2:
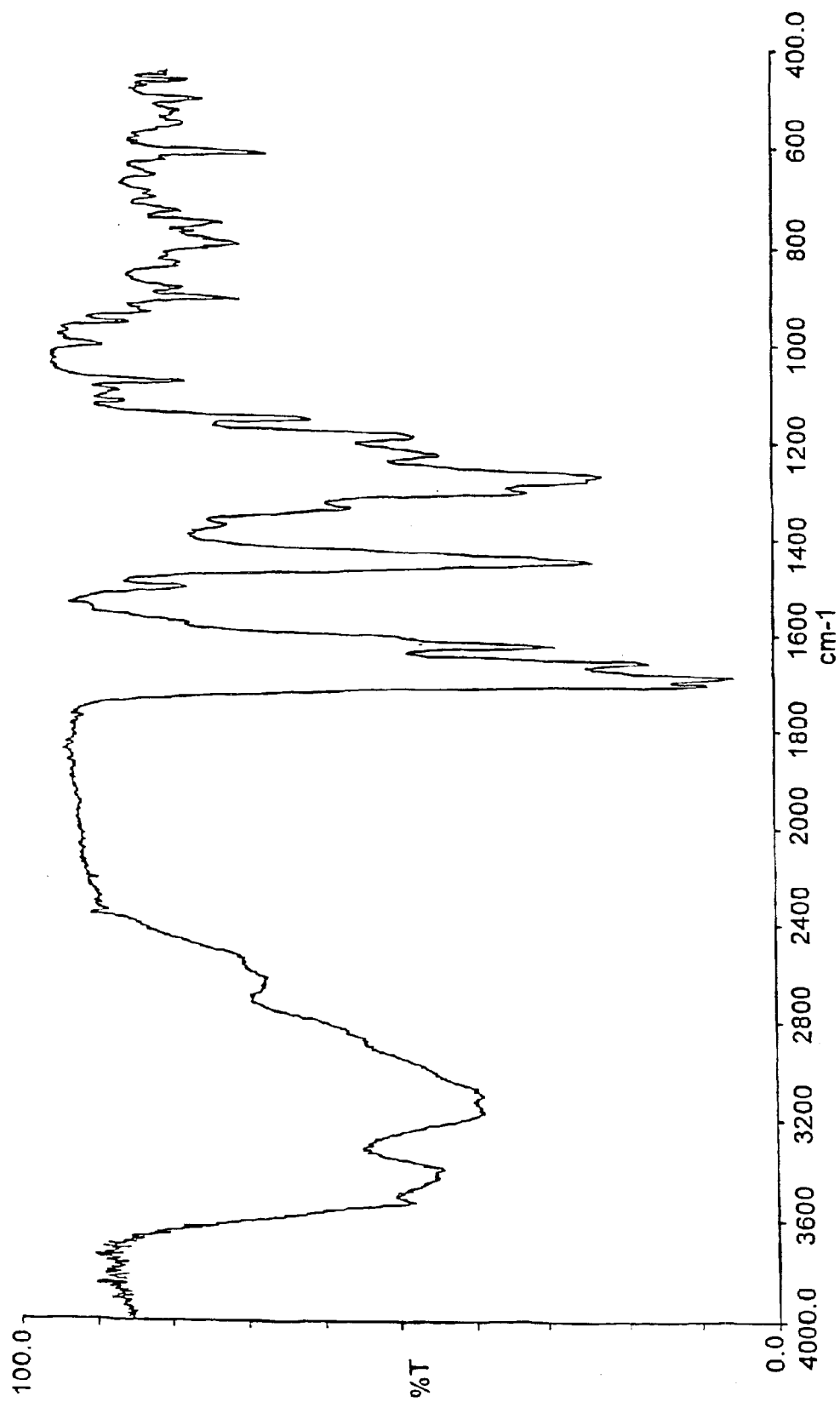
FIG. 2 is an infrared absorption spectrum (KBr) of the binaphthol derivative obtained in Example 2.

The infrared absorption spectrum (KBr) of the same is shown in FIG. 2.

EXAMPLE 3

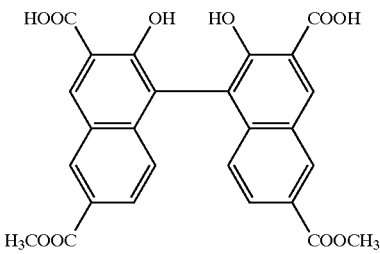

1.6 g of 1,1'-bis(2-hydroxy-3,6-dimethoxycarbonyl naphthalene) obtained in Example 1 was suspended in 20 g of N,N-dimethylformamide and 20 g of methanol, and 1.04 g of sodium bicarbonate in 20 g of water was added thereto. The mixture was reacted for 5–8 hours at 70–80° C. The filtrate was diluted with 40 g of water, the insoluble matter was removed and then, pH of the filtrate was adjusted to 2 with dilute hydrochloric acid. The precipitates were collected by filtration, washed well with water and methanol, and dried to give 1.39 g of the desired compound as pale yellow powder (MS: m/z 489(MW=490.4)).

EXAMPLES 4–15

According to the same manner as described in Example 1 with the exception that naphthol derivatives shown in table 1 were used instead of 2-hydroxy-3,6-dimethoxycarbonylnaphthalene, and the reacted solution was poured into 200 g of water, binaphthol compounds shown in table 1 were prepared. Mass spectroscopy data of the respective binaphthol derivatives are shown in table 1.

TABLE 1

| Example No. | naphthol derivative | binaphthol derivative | MS |
|---|---|---|---|
| 4 | (structure) | (structure) | m/z 761 |
| 5 | (structure) | (structure) | m/z 943 |
| 6 | (structure) | (structure) | m/z 974 |

TABLE 1-continued

| Example No. | naphthol derivative | binaphthol derivative | MS |
|---|---|---|---|
| 7 | | | m/z 724 |
| 8 | | | m/z 823 |
| 9 | | | m/z 861 |

TABLE 1-continued

| Example No. | naphthol derivative | binaphthol derivative | MS |
|---|---|---|---|
| 10 | (structure) | (structure) | m/z 1002 |
| 11 | (structure) | (structure) | m/z 822 |
| 12 | (structure) | (structure) | m/z 918 |

TABLE 1-continued

| Example No. | naphthol derivative | binaphthol derivative | MS |
|---|---|---|---|
| 13 | (structure) | (structure) | m/z 869 |
| 14 | (structure) | (structure) | m/z 1016 |

TABLE 1-continued
| Example No. | naphthol derivative | binaphthol derivative | MS |
|---|---|---|---|
| 15 | 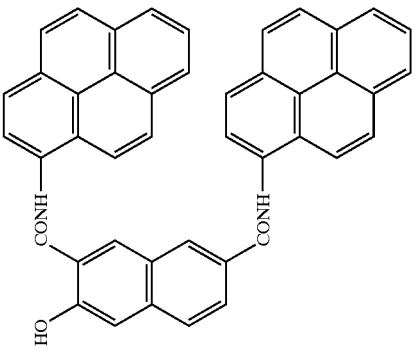 | 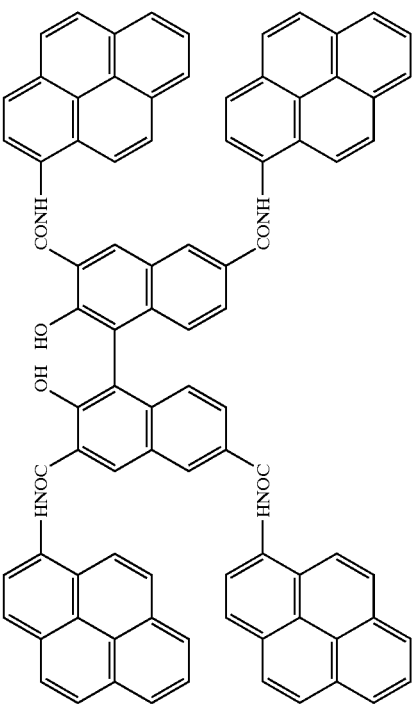 | m/z 1258 |

EXAMPLE 16

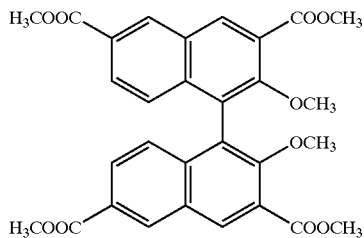

2.31 g of 1,1'-bis(2-hydroxy-3,6-dimethoxycarbonyl naphthalene) obtained in Example 1 was dispersed in 20 g of N,N-dimethylformamide, 2.84 g of methyl iodide and 2.07 g of potassium carbonate were added thereto. The mixture was reacted for 24 hours at about 40° C. After the reaction, the reaction mixture was poured into 100 g of water and the precipitates were collected by filtration. The precipitates were washed well with water and methanol, and dried to give 2.67 g of the desired compound as white powder. (melting point: 177° C., MS: m/z 546(MW=546.5))

Figure 3:
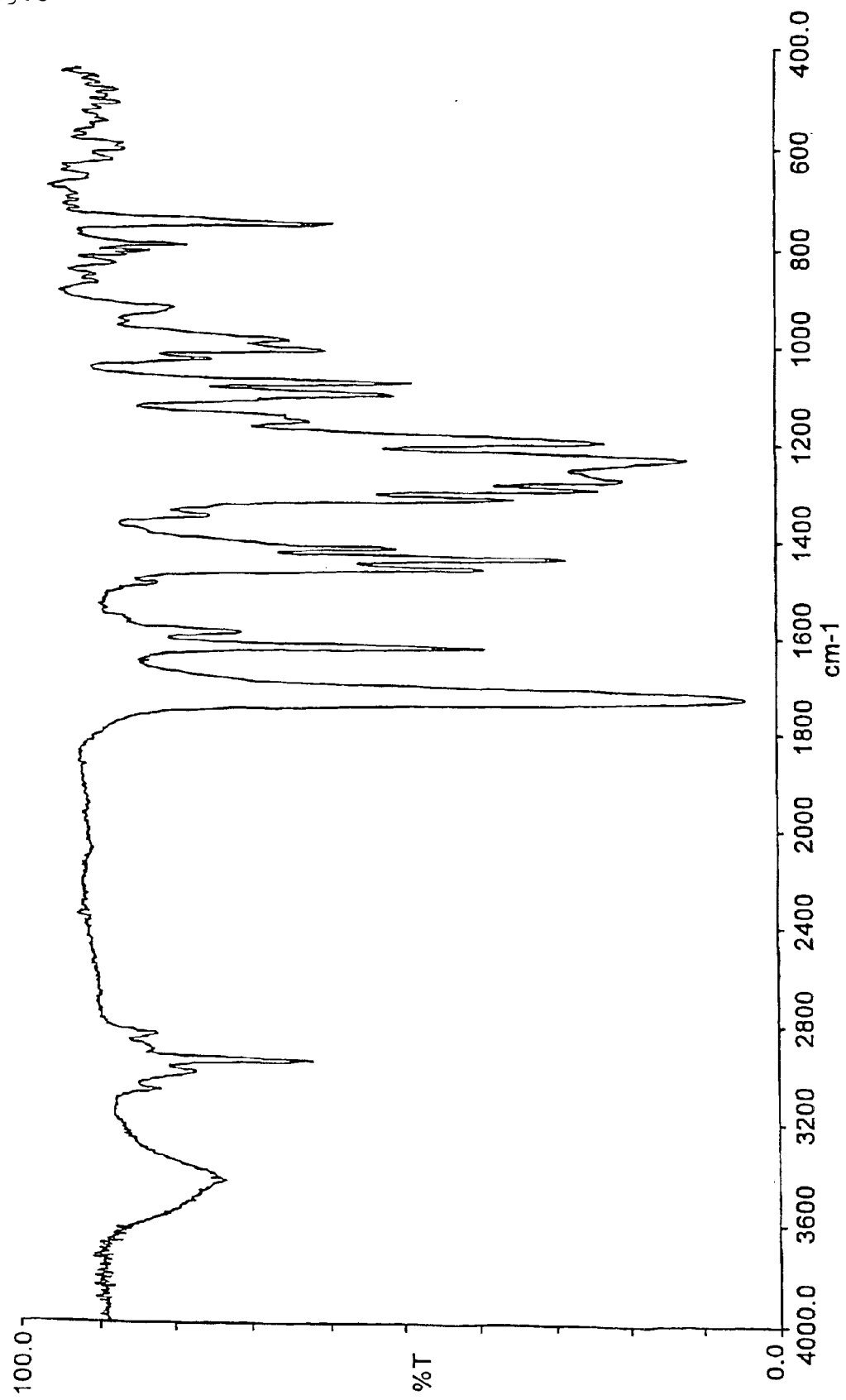
FIG. 3 is an infrared absorption spectrum (KBr) of the binaphthol derivative obtained in Example 16.

The infrared absorption spectrum (KBr) of the same is shown in FIG. 3.

EXAMPLE 17

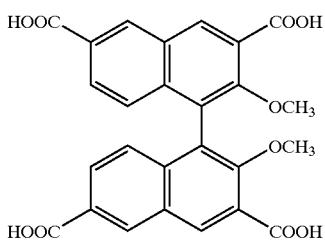

2.19 g of 1,1'-bis(2-methoxy-3,6-dimethoxycarbonyl naphthalene) obtained in Example 16 was dispersed in 20 g of methanol and 20 g of water, and 0.8 g of sodium hydroxide was added thereto. The mixture was reacted for 5 hours at about 60° C. After that, insoluble matters were removed by filtration and the filtrate was diluted with 100 g of water. PH value of the filtrate was adjusted to 2 with dilute hydrochloric acid, and the precipitates were collected by filtration. The precipitates were washed well with water and methanol and dried to give 1.86 of the desired compound as white powder. (decomposition point: 330° C., MS: m/z 489(MW=490.4).

Figure 4:
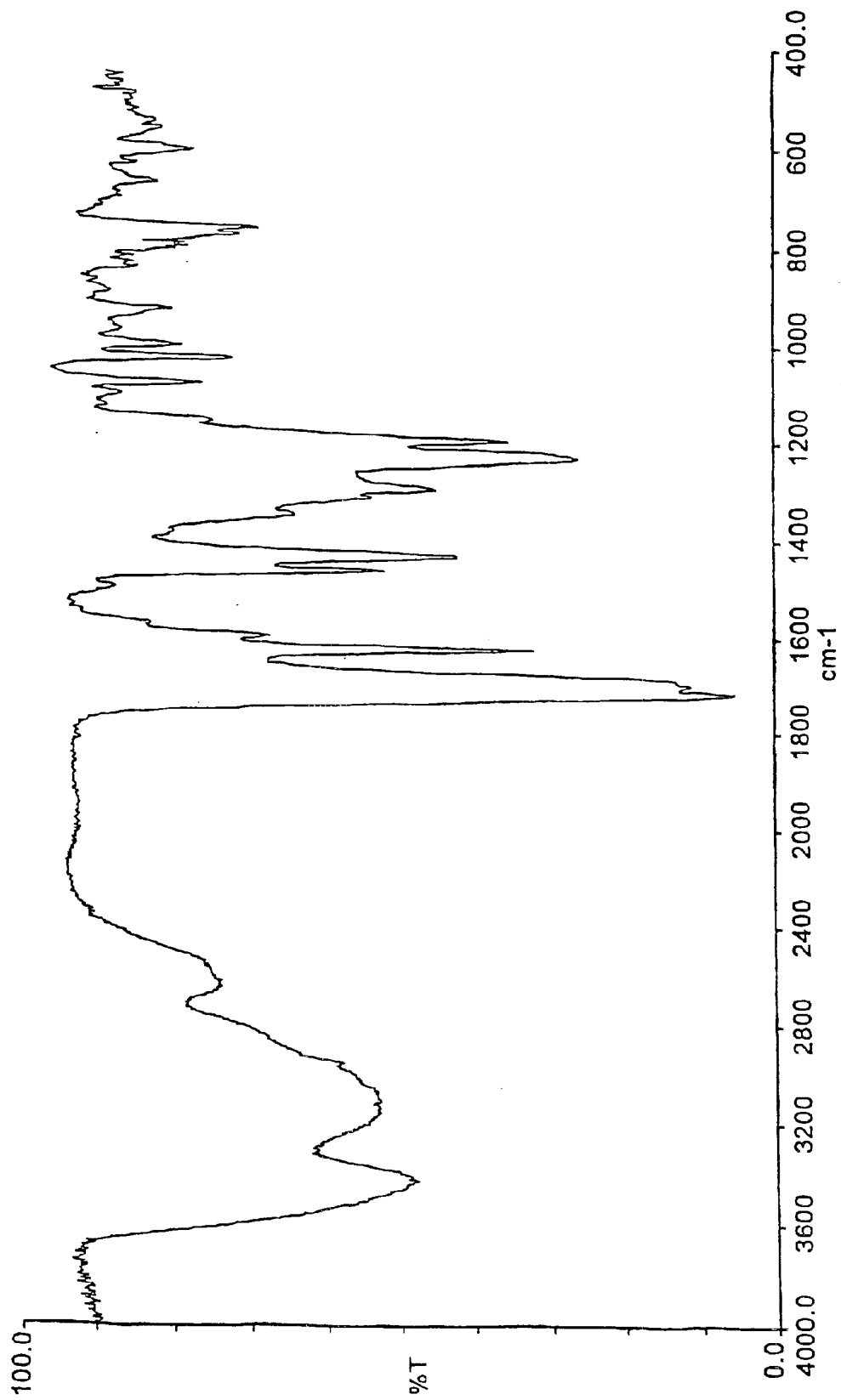
FIG. 4 is an infrared absorption spectrum (KBr) of the binaphthol derivative obtained in Example 17.

The infrared absorption spectrum (KBr) of the same is shown in FIG. 4.

EXAMPLE 18

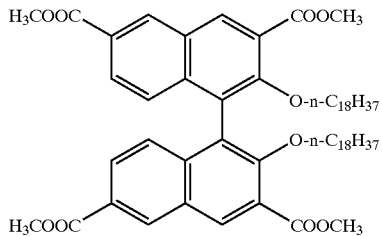

2.31 g of 1,1'-bis(2-hydroxy-3,6-dimethoxycarbonyl naphthalene) obtained in Example 1 was dispersed in 40 g of N,N-dimethylformamide, and 3.82 g of octadecane bromide and 1.66 g of potassium carbonate were added thereto. The mixture was reacted for 18 hours at about 80° C. After that, the reaction mixture was poured into 200 g of water and the precipitates were collected by filtration. The precipitates were washed well with water and methanol, and dried to give 5.01 g of the desired compound as white powder. (melting point: 41–45° C., decomposition point: 380° C., MS: m/z 1023 (MW=1023.4)).

Figure 5:
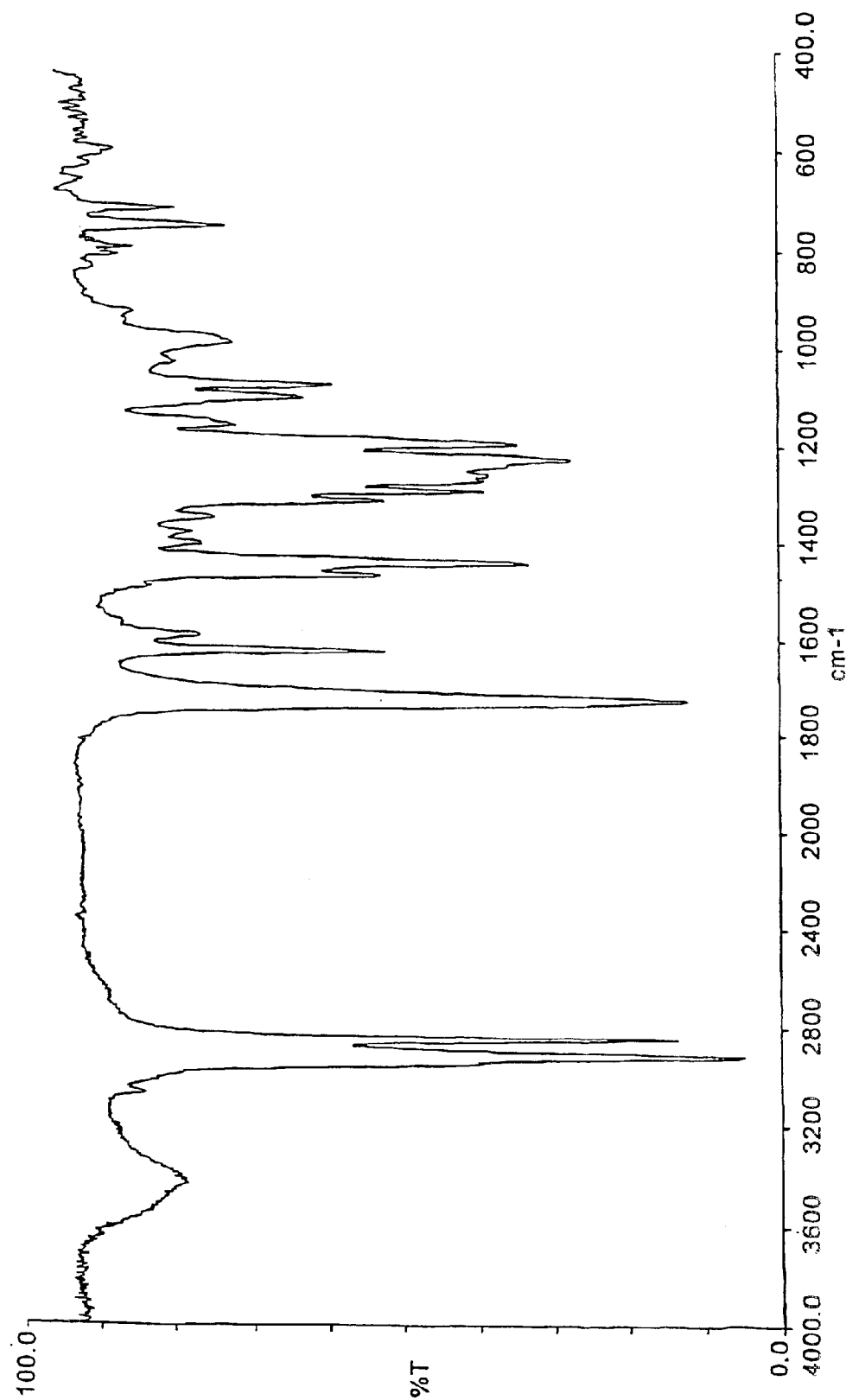
FIG. 5 is an infrared absorption spectrum (KBr) of the binaphthol derivative obtained in Example 18.

The infrared absorption spectrum (KBr) of the same is shown in FIG. 5.

EXAMPLE 19

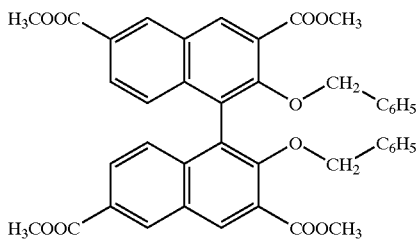

2.31 g of 1,1'-bis(2-hydroxy-3,6-dimethoxycarbonyl naphthalene) obtained in Example 1 was dispersed in 30 g of N,N-dimethylformamide, 1.39 g of benzyl chloride and 1.66 g of potassium carbonate were added thereto. The mixture was reacted for 18 hours at about 80° C. After that, the reaction mixture was poured into 100 g of water and the precipitates were collected by filtration. The precipitates were washed well with water and methanol, and dried to give 3.39 g of the desired compound as white powder. (melting point: 160–165° C., decomposition point: 305° C., MS: m/z 698 (MW=698.7)).

Figure 6:
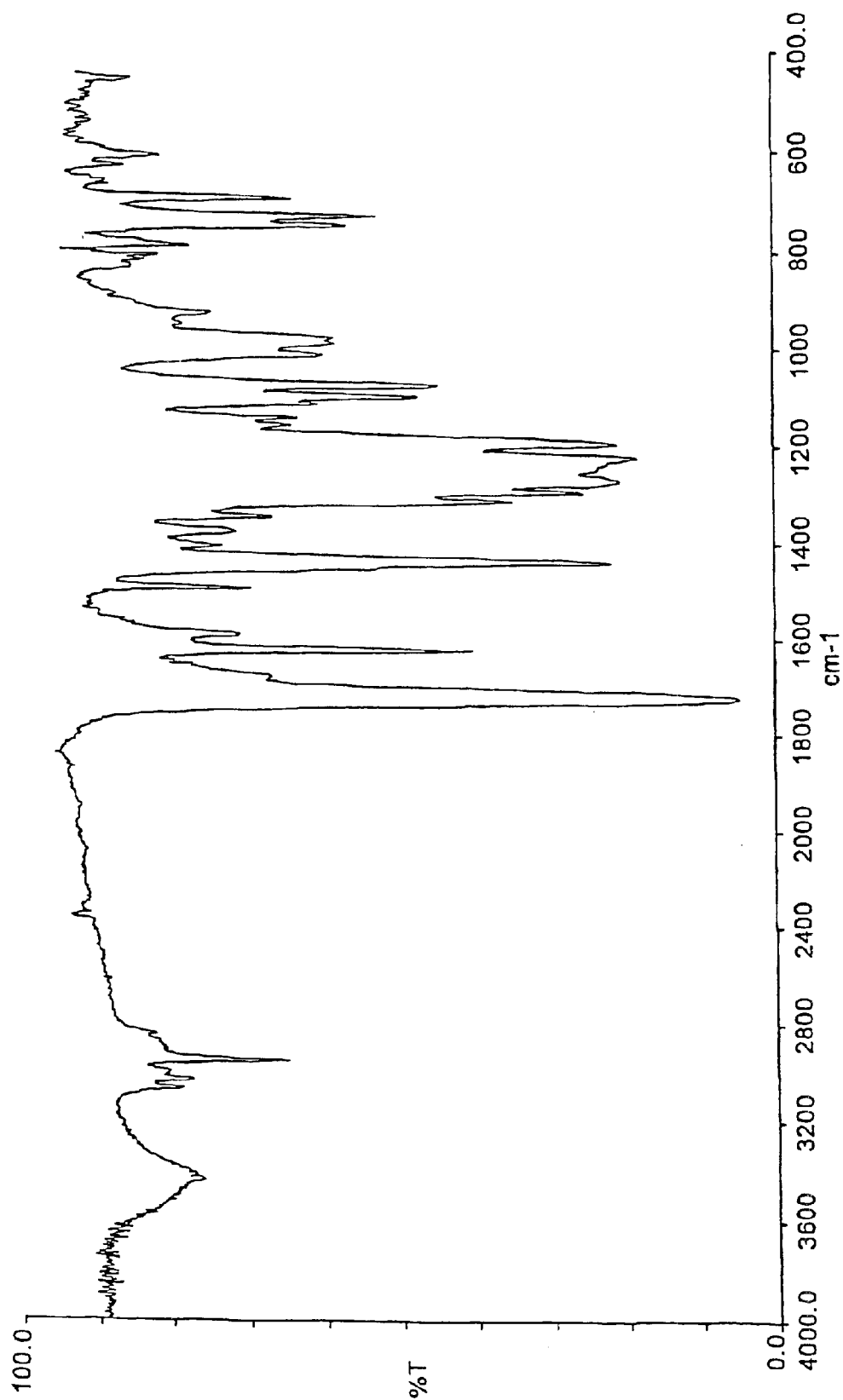
FIG. 6 is an infrared absorption spectrum (KBr) of the binaphthol derivative obtained in Example 19.

The infrared absorption spectrum (KBr) of the same is shown in FIG. 6.

EXAMPLE 20

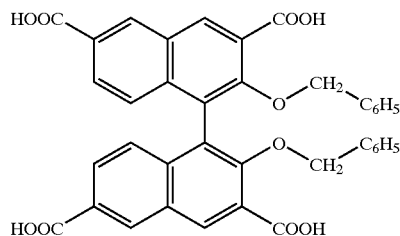

2.79 g of 1,1'-bis(2-benzyloxy-3,6-dimethoxycarbonyl naphthalene) obtained in Example 19 was dispersed in 20 g of methanol and 20 g of water, and 0.8 g of sodium hydroxide was added thereto. The mixture was reacted for 5 hours at about 60° C. After that, insoluble matters were removed from the reaction mixture and the mixture was diluted with 100 g of water. The pH of the mixture was adjusted to 2 with dilute hydrochloric acid and the precipitates were collected by filtration. The precipitates were washed well with water and methanol, and dried to give 2.26 g of the desired compound as white powder (MS: m/z 641 (MW=642.6)).

EXAMPLE 21

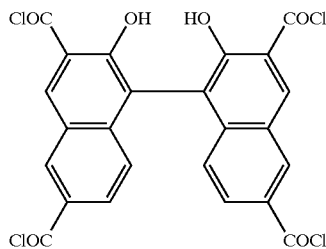

2.31 g of 1,1'-bis(2-hydroxy-3,6-dihydroxycarbonyl naphthalene) obtained in Example 2 was dispersed in 20 g of tetrahydrofuran, 3.6 g of thionyl chloride was added thereto, and the mixture was reacted for 8 hours at about 50° C. After that, tetrahydrofuran and the excess thionyl chloride were removed by evaporation to give 2.73 g of the desired acid chloride compound.

Figure 7:
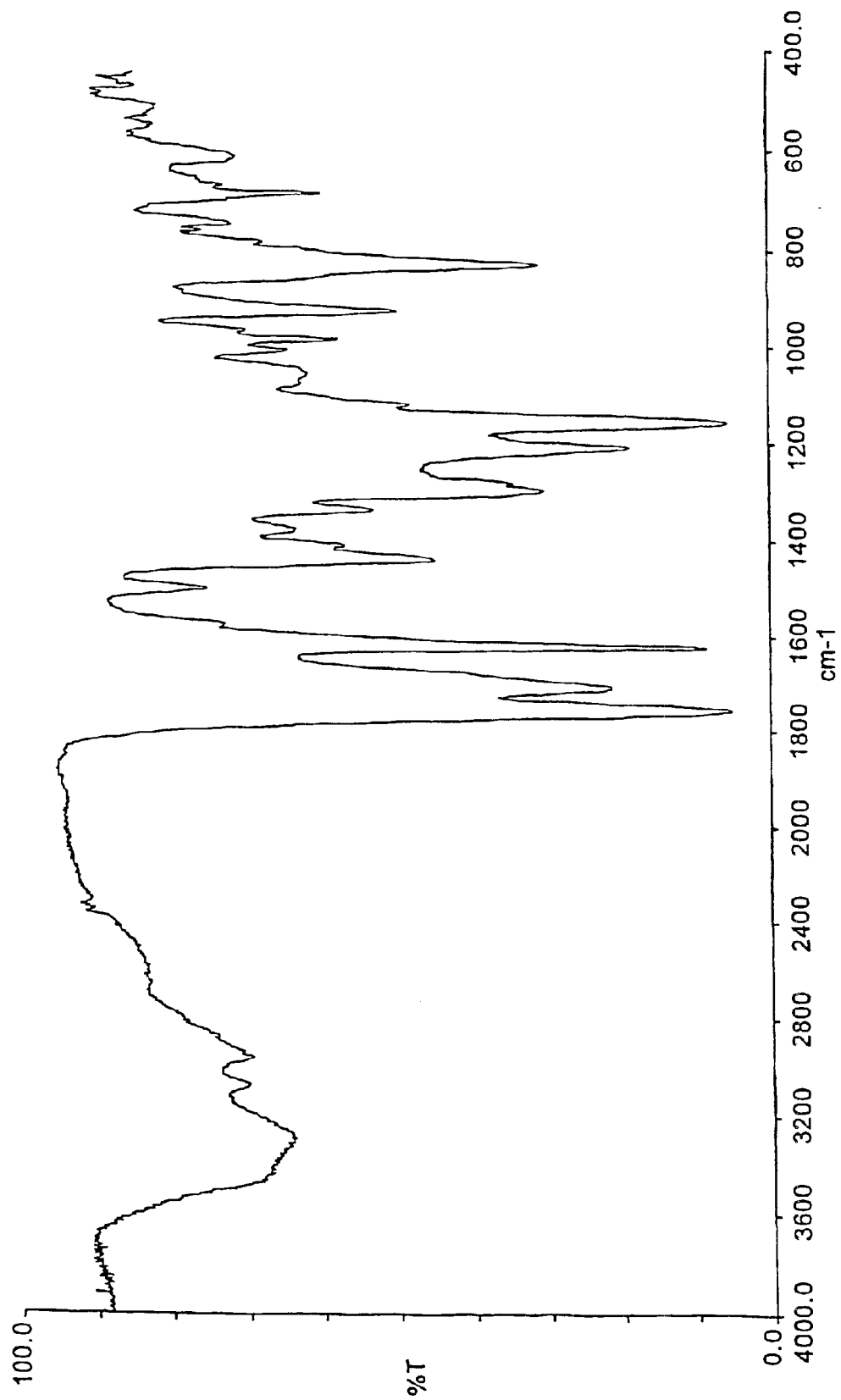
FIG. 7 is an infrared absorption spectrum (KBr) of the binaphthol derivative obtained in Example 21.

The infrared absorption spectrum (KBr) of the same is shown in FIG. 7.

EXAMPLE 22

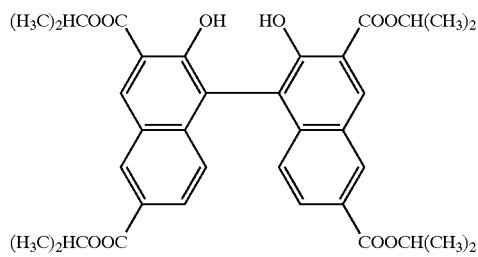

2.68 g of 1,1'-bis(2-hydroxy-3,6-dichlorocabonyl naphthalene) obtained in Example 21 was dissolved in 10 g of tetrahydrofuran, 10 g of isopropyl alcohol was added thereto and the mixture was reacted for about 2 hours under reflux. After that, the reaction mixture was cooled to the room temperature and the precipitates were collected by filtration. The precipitates were vacuum dried to give 1.98 g of the desired isopropyl ester compound as pale yellow powder. (decomposition point: 299° C.)

Figure 8:
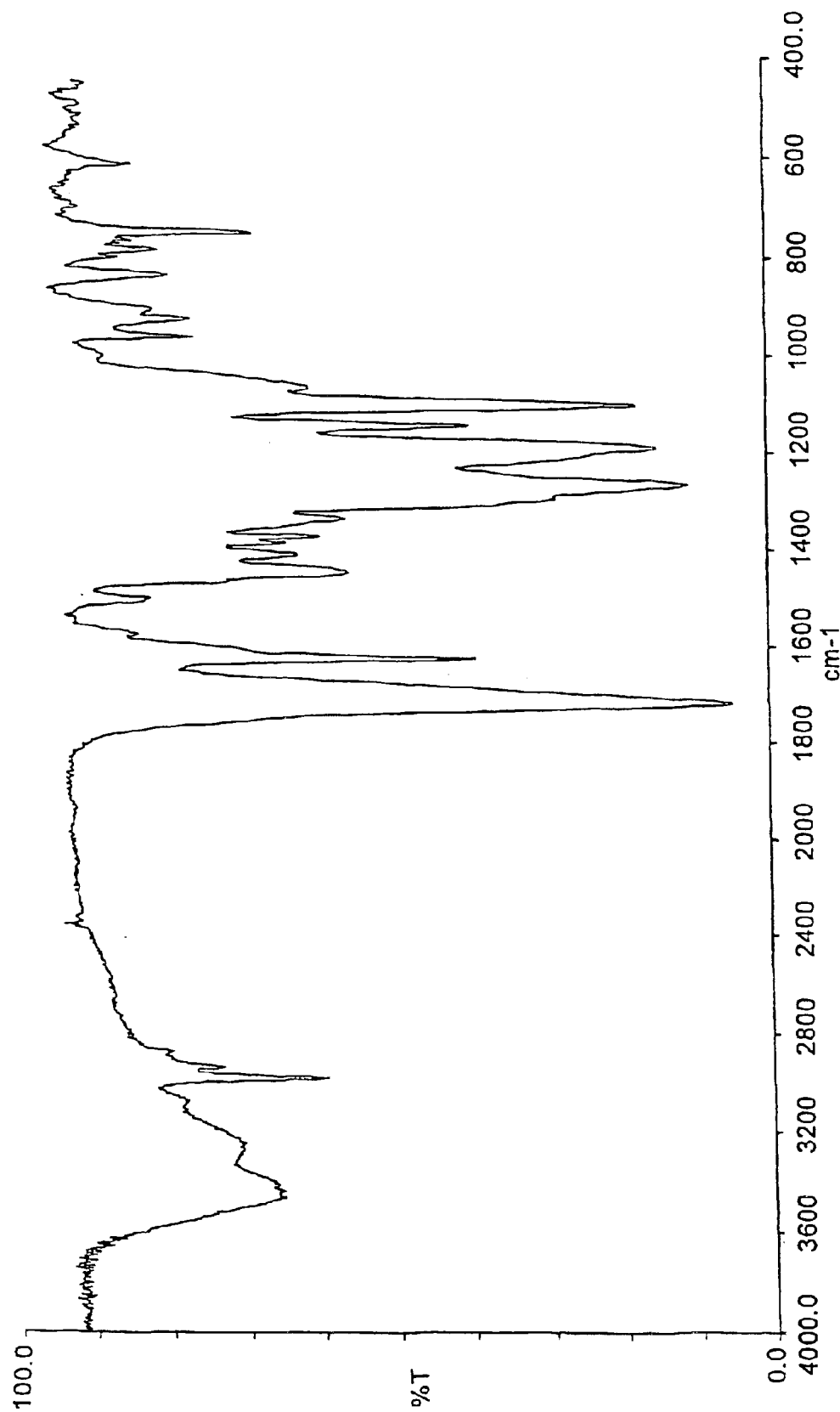
FIG. 8 is an infrared absorption spectrum (KBr) of the binaphthol derivative obtained in Example 22.

The infrared absorption spectrum (KBr) of the same is shown in FIG. 8.

EXAMPLE 23

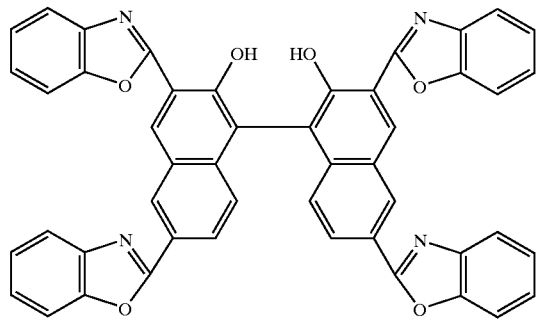

2.31 g of 1,1'-bis(2-hydroxy-3,6-dimethoxycarbonyl naphthalene) obtained in Example 1 was dispersed in 50 g of sulfolane, and 2.73 g of 2-aminophenol and 0.55 g of phosphorous trichloride were added thereto. The mixture was heated to about 140° C. and then reacted for about 24 hours. After that, the reaction mixture was poured into 200 g of water and the precipitates were collected by filtration. The precipitates were washed well with water and methanol and dried to give 3.22 g of the desired compound (MS: m/z 753 MW=754.7)).

EXAMPLE 24

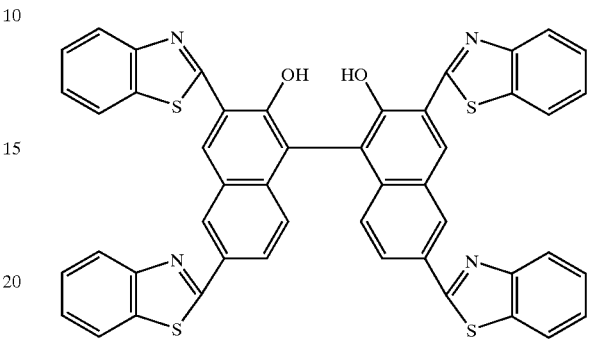

2.31 g of 1,1'-bis(2-hydroxy-3,6-dimethoxycarbonyl naphthalene) obtained in Example 1 was dispersed in 50 g of sulfolane and 3.13 g of 2-aminobenzene thiol and 0.55 g of phosphorous trichloride were added thereto. The mixture was heated to about 140° C. and reacted for 24 hours. After that, the reaction mixture was poured into 200 g of water and the precipitates were collected by filtration. The precipitates were washed well with water and methanol and dried to give 3.22 g of the desired compound as white powder (MS: m/z 818 (MW=819.0)

Industrial Applicability

The binaphthol derivative of the present invention is useful for manufacturing antiseptic compounds or chiral catalysts. According to the method of the present invention, binaphthol derivatives can be prepared in high yield with low cost.

What is claimed is:

1. A binaphthol derivative represented by the formula [1]:

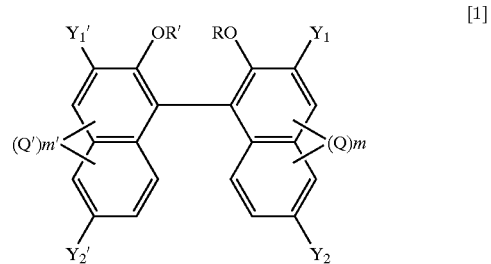

[1]

wherein $Y_1$, $Y_1'$, $Y_2$, and $Y_2'$ may be same or different and each is selected from the group consisting of a carboxyl group, an esterified carboxyl group, a group of —(CONH)n-X (wherein X is an optionally branched and optionally substituted hydrocarbon group which may have an unsaturated bond, an optionally substituted aromatic group or a heterocyclic group having conjugated double bonds, n is an integer of 1 or 2), and a group of formula [2]

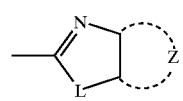

[2]

wherein L is —O—, —S— or —NH—, and Z is an optionally substituted aromatic group or a heterocyclic group having conjugated double bonds;

R and R' are selected from the group consisting of hydrogen atom, an alkaline metal, an optionally branched and optionally substituted alkyl group of 1–20 carbon atoms, an acyl group and a phenylalkylene group;

Q and Q' are selected from the group consisting of optionally branched alkyl and alkoxy group of 1–6 carbon atoms, a halogen atom, nitro group and nitroso group; and m and m' each represents an integer of 0–3 or a salt thereof.

2. A binaphthol derivative of claim 1, wherein the binaphthol derivative is represented by formula [3]

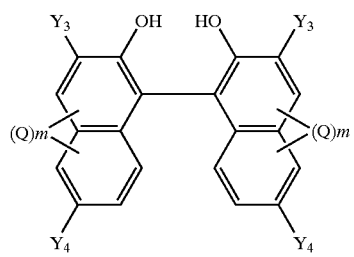

[3]

wherein $Y_3$ and $Y_4$ may be same or different and each is independently selected from the group consisting of an esterified carboxyl group and a group of —(CONH)n-X, wherein X and n are the same as defined in claim 1; and Q and m are the same as defined in claim 1.

3. A binaphthol derivative of claim 1, wherein the binaphthol derivative is represented by formula [4]:

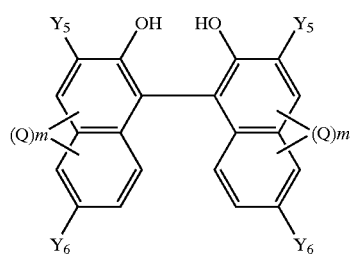

[4]

wherein one of $Y_5$ and $Y_6$ is a carboxyl group and the other is selected from the group consisting of a carboxyl group, an esterified carboxyl group and a group of —(CONH)n-X (wherein X and n are the same as defined in claim 1); and Q and m are the same as defined in claim 1.

4. A method for preparing a binaphthol derivative, wherein the binaphthol derivative is a binaphthol derivative of claim 2 represented by formula [3]

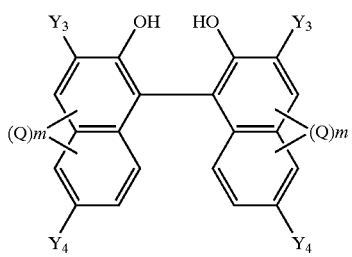

[3]

wherein $Y_3$, $Y_4$, Q and m are the same as defined in claim 2, comprising carrying out an oxidative coupling reaction of a naphthol derivative represented by formula [5]:

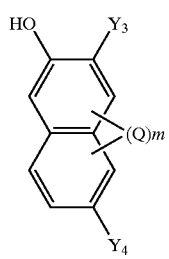

[5]

wherein $Y_3$, $Y_4$, Q and m are the same as defined above in a nitrogen containing polar solvent in the presence of a copper salt.

5. The method of claim 4, wherein the copper salt is copper (I) chloride.

6. The method of claim 5, wherein the oxidative coupling reaction is carried out in the presence of oxygen.

7. The method of claim 4, wherein the nitrogen containing polar solvent is selected from the group consisting of those represented by formulae [6] and [7]:

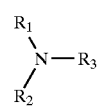

[6]

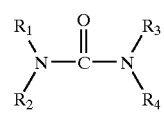

[7]

wherein $R_1$, $R_2$, $R_3$ and $R_4$ may be same or different and each independently selected from the group consisting of formyl, alkyl, alkenyl, acyl and optionally substituted phenyl groups.

8. The method of claim 7, wherein the nitrogen containing polar solvent is selected from the group consisting of N,N-dimethylformamide, N,N-dimethyl acetamide, N-methyl-2-pyrrolidone, morpholine, N-methylmorpholine, N,N-diethylacetamide, N,N-dimethyl propylamide, tetraethylurea, tetraethylurea, N-methyl acetanilide, N,N-dimethylaniline, N,N-dimethylanisidine, pyridine, and 2-methylpyridine.

9. The method of claim 4, wherein the nitrogen containing polar solvent is selected from the group consisting of N,N-dimethylformamide, N,N-dimethyl acetamide and N-methyl-2-pyrrolidone.

10. A method for preparing a naphthol derivative represented by formula [4]:

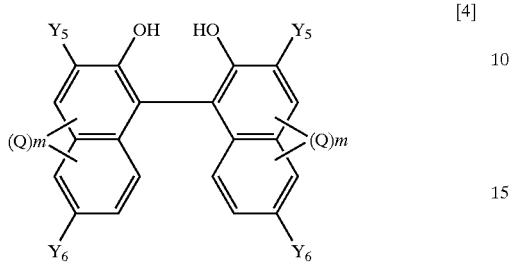

[4]

wherein one of $Y_5$ and $Y_6$ is a carboxyl group and the other is selected from the group consisting of a carboxyl group, an esterified carboxyl group and a group of —(CONH)n-X (wherein X is an optionally branched and optionally substituted hydrocarbon group which may have an unsaturated bond, an optionally substituted aromatic group or a heterocyclic group having conjugated double bonds, n is an integer of 1 or 2), Q is selected from the group consisting of optionally branched alkyl and alkoxy group of 1–6 carbon atoms, a halogen atom, nitro group and nitroso group, and m represents an integer of 0–3, comprising hydrolyzing a binaphthol derivative represented by formula [3]:

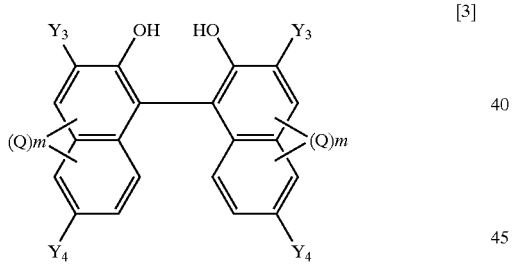

[3]

wherein $Y_3$ and $Y_4$ may be same or different and each is independently selected from the group consisting of an esterified carboxyl group and a group of —(CONH)n-X (wherein X is an optionally branched and optionally substituted hydrocarbon group which may have an unsaturated bond, an optionally substituted aromatic group or a heterocyclic group having conjugated double bonds, n is an integer of 1 or 2), Q is selected from the group consisting of optionally branched alkyl and alkoxy group of 1–6 carbon atoms, a halogen atom, nitro group and nitroso group, and m represents an integer of 0–3, provided that $Y_3$ and $Y_4$ are not —(CONH)n-X at the same time.

11. The method of claim 10, wherein the hydrolyzing reaction is carried out in a basic solution.

12. A binaphthol derivative of claim 1, wherein the binaphthol derivative is an optically active binaphthol derivative selected from the group consisting of compounds represented by formula [8]:

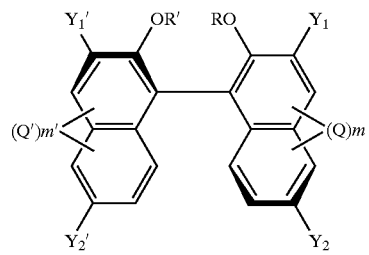

[8]

and formula [9]:

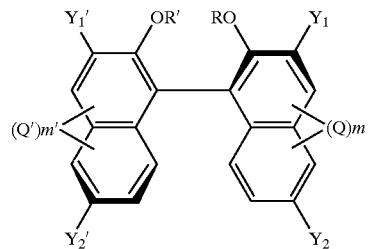

[9]

wherein $Y_1$, $Y_1'$, $Y_2$, $Y_2'$, R, R', Q, Q', m and m' are the same as defined in claim 1.

13. A method for preparing a binaphthol derivative, wherein the binaphthol derivative is a binaphthol derivative of claim 12 selected from the compounds represented by formulae [8] and [9], wherein said method comprises optically resolving a binaphthol derivative represented by formula [1] by means of high performance liquid chromatography with an optically active column:

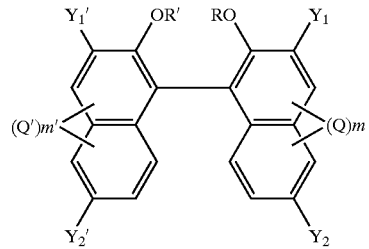

[1]

wherein $Y_1$, $Y_1'$, $Y_2$, and $Y_2'$ may be same or different and each is selected from the group consisting of a carboxyl group, an esterified carboxyl group, a group of —(CONH)n-X (wherein X is an optionally branched and optionally substituted hydrocarbon group which may have an unsaturated bond, an optionally substituted aromatic group or a heterocyclic group having conjugated double bonds, n is an integer of 1 or 2), and a group of formula [2]

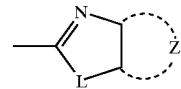

[2]

wherein L is —O—, —S— or —NH—, and Z is an optionally substituted aromatic group or a heterocyclic group having conjugated double bonds;

R and R' are selected from the group consisting of hydrogen atom, an alkaline metal, an optionally branched and optionally substituted alkyl group of 1–20 carbon atoms, an acyl group and a phenylalkylene group;

Q and Q' are selected from the group consisting of optionally branched alkyl and alkoxy group of 1–6 carbon atoms, a halogen atom, nitro group and nitroso group; and m and m' each represents an integer of 0–3.

* * * * *